(12) United States Patent
Bjellqvist et al.

(10) Patent No.: US 8,858,771 B2
(45) Date of Patent: Oct. 14, 2014

(54) GEL FOR ISOELECTRIC FOCUSING

(75) Inventors: Bengt Bjellqvist, Uppsala (SE); Kristina Uhlen, Uppsala (SE)

(73) Assignee: GE Healthcare Bio-Sciences AB, Uppsala (SE)

( * ) Notice: Subject to any disclaimer, the term of this patent is extended or adjusted under 35 U.S.C. 154(b) by 0 days.

(21) Appl. No.: 13/370,362

(22) Filed: Feb. 10, 2012

(65) Prior Publication Data

US 2012/0138464 A1 Jun. 7, 2012

Related U.S. Application Data

(63) Continuation of application No. 12/096,815, filed as application No. PCT/SE2006/001449 on Dec. 19, 2006, now abandoned.

(30) Foreign Application Priority Data

Dec. 22, 2005 (SE) ..................................... 0502911

(51) Int. Cl.
*G01N 27/447* (2006.01)
*C07K 1/28* (2006.01)

(52) U.S. Cl.
CPC ............ *C07K 1/28* (2013.01); *G01N 27/44795* (2013.01); *G01N 27/44747* (2013.01)
USPC ..... 204/459; 435/287.1; 422/68.1; 422/82.01

(58) Field of Classification Search
USPC .............. 204/450–462; 435/23, 24, 195, 199, 435/212, 213; 436/178, 86, 87, 94, 436/173–175
See application file for complete search history.

(56) References Cited

U.S. PATENT DOCUMENTS

2005/0087445 A1 4/2005 Speicher et al.
2005/0202405 A1* 9/2005 Amshey et al. .................. 435/4

FOREIGN PATENT DOCUMENTS

JP 11 00448 4/1989
WO WO 2005/026715 3/2005

OTHER PUBLICATIONS

Patterson et al. (Proteomics: the first decade and beyond, 2003; Nat Genet 33 Suppl: 311-23).*
Cargile et al. (Journal of Biomolecular Techniques, vol. 16, issue 3, Sep. 2005).*
Poznanovic et al., Electrophoresis, Aug. 2005, 26, 3185-3190.*
Bunai et al. (Journal of Chromatography B, 815 (2005) 227-236).*
Amersham Article (http://juang.bst.ntu.edu.tw/Protein/proteomics/files/IPGphor%20ll.pdf, on web 2003).*
Cossu et al. (Journal of Chromatography, 361 (1986) 223-229).*
Johansson, H.-O., et al., Biotechnology and Bioengineering, 66(4), 247-257, 1999.
Nilsson, et al., Biochimica et Biophysica Acta, 1601, 138-148, 2002.
Persson, J., et al., Bioseparation 9, 105-116, 2000.
Patent Abstracts of Japan, vol. 0133, No. 41, Jul. 31, 1989.
Gianazza, E., et al., Electrophoresis, 6, 53-56, 1985.
Zuo, X., et al., Proteomics, 2, 58-68, 2002.
Bjellqvist, B., et al., Electrophoresis, 15, 529-539, 1994.
Farhoud, et.al. Jounral of Proteome Research Vo. 4, No. 6, Oct. 8, 2005 pp. 2364-2368.
EP 06835869 Search Report Dated Oct. 23, 2013.

* cited by examiner

*Primary Examiner* — Jennifer Dieterle

(57) ABSTRACT

The present invention relates to the field of electrophoresis and more specifically to a gel or strip for separating peptide components by isoelectric focusing by producing IPG (immobilized pH gradient) gels or strips in a novel way before focusing. More closely, the peptides are focused in a novel IPG gel including an uneven or non-linear pH gradient having at least three separate stepwise arranged pH-intervals. After focusing the peptide resolution is high and the peptides are evenly distributed along the gel.

6 Claims, 3 Drawing Sheets

GEL FOR ISOELECTRIC FOCUSING

CROSS-REFERENCE TO RELATED APPLICATIONS

This application is a continuation of U.S. patent application Ser. No. 12/096,815 filed Jun. 10, 2008, which is a filing under 35 U.S.C. §371 and claims priority to international patent application number PCT/SE2006/001449 filed Dec. 19, 2006, published on Jun. 28, 2007, as WO 2007/073293, which claims priority to patent application number 0502911-1 filed in Sweden on Dec. 22, 2005.

FIELD OF THE INVENTION

The present invention relates to the field of electrophoresis and more specifically to a gel or strip for separating peptide components by isoelectric focusing by producing IPG (immobilised pH gradient) gels or strips in a novel way. More closely, the peptides are focused in a novel IPG gel comprising an uneven or non-linear pH gradient comprising at least three separate pH-intervals.

BACKGROUND OF THE INVENTION

The isolation and separation of biomolecules, such as proteins and peptides, has become of an increased interest during the past years. Some biomolecules need to be isolated as a last step of a biotechnological method for the production thereof, for example in the preparation of protein or peptide-based pharmaceutical compounds. Similarly there is also a need to separate biomolecules for analytical purposes in order to be able to quantify and identify the proteins and/or peptides present in a sample. Electrophoretic methods are commonly used in the separation step. A wide variety of methods are used for the detection and quantification of the separated proteins and/or peptides. For identification and characterisation of separated proteins mass spectrometry (MS) methods are normally used as these methods are fast and require very small amounts of proteins and/or peptides.

In isoelectric focusing (IEF), the separation takes place in a pH gradient that occupies the whole separation distance and is arranged so that the pH in the gradient increases from anode towards the cathode. While other alternatives also exist, the pH gradients required in isoelectric focusing are in practice generated in two different ways: with the aid of a solution of carrier ampholytes or with an immobilised pH gradient.

In the case of an immobilised pH gradient (IPG) the charged or chargeable groups generating the pH gradient are bound either to the wall of a capillary system or to the matrix when some kind of gel is used to get convection stabilisation. The immobilised charged or chargeable groups used are normally a limited number of carboxylic groups or amino groups with different pK-values distributed within or close to the pH gradient, which is to be generated. The concentration of the charged or chargeable groups is varied along the separation distance in a manner causing the pH at which the wall or the gel matrix has a zero net charge to increase from the anode to the cathode. A commercially available example of a system for generation of immobilised pH gradients is the IMMO-BILINE II SYSTEM™ (Amersham Biosciences, Uppsala, Sweden), wherein a pH gradient covalently attached to a polyacrylamide gel is formed. Immobilised pH gradients are truly stationary and today they are normally used together with carrier ampholytes. In this combination the immobilised gradient determines the resulting pH gradient, while the carrier ampholytes contribute with conductivity.

A common problem with isoelectric focusing of proteins and/or peptides is that the focused proteins/peptides are unevenly distributed in the gel with bad resolution.

To solve this problem for proteins, a non-linear pH-gradient has been immobilised in IEF gels, for example IMMO-BILINE DRYSTRIPS™ pH 3-11 NL (Amersham Biosciences, Uppsala, Sweden). This non-linear gradient cannot be used for focusing of peptides.

JP 1100448 A describes arranging several gel media in parallel relative to the direction of migration of proteins in isoelectric focusing. The gel media each comprise a different pH-range. Thus, this invention does not describe a continuous gel having a step-wise pH-gradient in the same gel. Furthermore, it does not describe focusing of peptides.

Thus, there is a need of improved gels or strips for isoelectric focusing of peptides with better resolution and distribution of the peptides after focusing.

SUMMARY OF THE INVENTION

The present invention provides an optimal immobilised pH gradient in IEF gels for peptide separation resulting in even distribution and high resolution of peptides in the gel in which the separation has been done. Each IEF-gel comprises a non-linear step-wise pH-gradient arranged in a continuous gel.

The present inventors have found that the peptide distribution in a given sample depends to some extent on the origin of the proteins from which the peptides are generated, but the main factors influencing the distribution is the digestion approach used for the generation of the peptides and possible modifications introduced for mass tagging. The present invention provides a pH gradient optimal to be used with peptides generated with tryptic digestion and describes how this pH gradient can be used.

The IEF gels according to the invention may be produced using available pI prediction programs allowing optimised gradients for different types of peptide samples (Bjellqvist B, Basse B, Olsen E, Celis J E. Reference points for comparisons of two-dimensional maps of proteins from different human cell types defined in a pH scale where isoelectric points correlate with polypeptide compositions. Electrophoresis. 1994 March-April; 15(3-4):529-39).

Thus, in a first aspect the present invention provides a gel for isoelectric focusing of peptides comprising a non-linear immobilised pH gradient having at least 3 separate stepwise arranged pH-intervals, wherein the peptides are evenly distributed along the gel after isoelectric focusing. The invention also provides a method comprising loading peptide samples on gel for isoelectric focusing of peptides comprising a non-linear immobilised pH gradient having at least 3 separate stepwise arranged pH-intervals, wherein the peptides are evenly distributed along the gel after isoelectric focusing.

The three pH-intervals are not overlapping and not immediately adjacent each other and are separated from each other by a pH-gap. For example, the gel comprises an immobilised pH gradient in the following pH-intervals pH 3.4-5.0, pH 5.2-6.8, and pH 7.8-10. Peptides with the corresponding approximate pI-values will focus in these three pH-intervals. Preferably, the peptides are generated by tryptic digestion of proteins, i.e. by digestion with the enzyme trypsin.

When using the gel of the invention, the peptides will focus with high resolution in the gel. Furthermore, the peptides will be evenly spread in the pH-gradient.

In one embodiment, the gel comprises three separate gel pieces each representing the separate stepwise pH-intervals, wherein the three pieces are joined together to form a continuous gel.

The gel may be pre-swollen or pre-cast to a conventional wet thickness.

Alternatively, the gel is in a dried condition. In this case, the gel is preferably rehydrated to less than its original thickness before use. Preferably the gel is rehydrated to 40-90% of its original thickness, more preferably 55-65%. The thinner gels have even higher resolution than the gels of the original wet thickness. Moreover, the thinner gels show decreased diffusion of peptides after focusing.

In a second aspect, the invention provides a kit comprising a dried or pre-cast IEF gel and a sample bridge comprising urea or other denaturant. The sample bridge is provided between one end of the gel and one of the electrodes, i.e. cathode or anode, and is used for loading of sample onto the gel. The sample bridge could be made of any suitable material, such as conventional paper bridge or hydrogel gel, such as acrylamide or agarose. The sample bridge is preferably saturated a high denaturant concentration, such as with 8M urea, and is provided on the anodic side of the IEF gel during focusing. The type of denaturant is dependent on the type of denaturant used in the gel. This sample bridge prevents depletion of denaturant from the IEF strip.

DETAILED DESCRIPTION OF THE INVENTION

Figure 1:
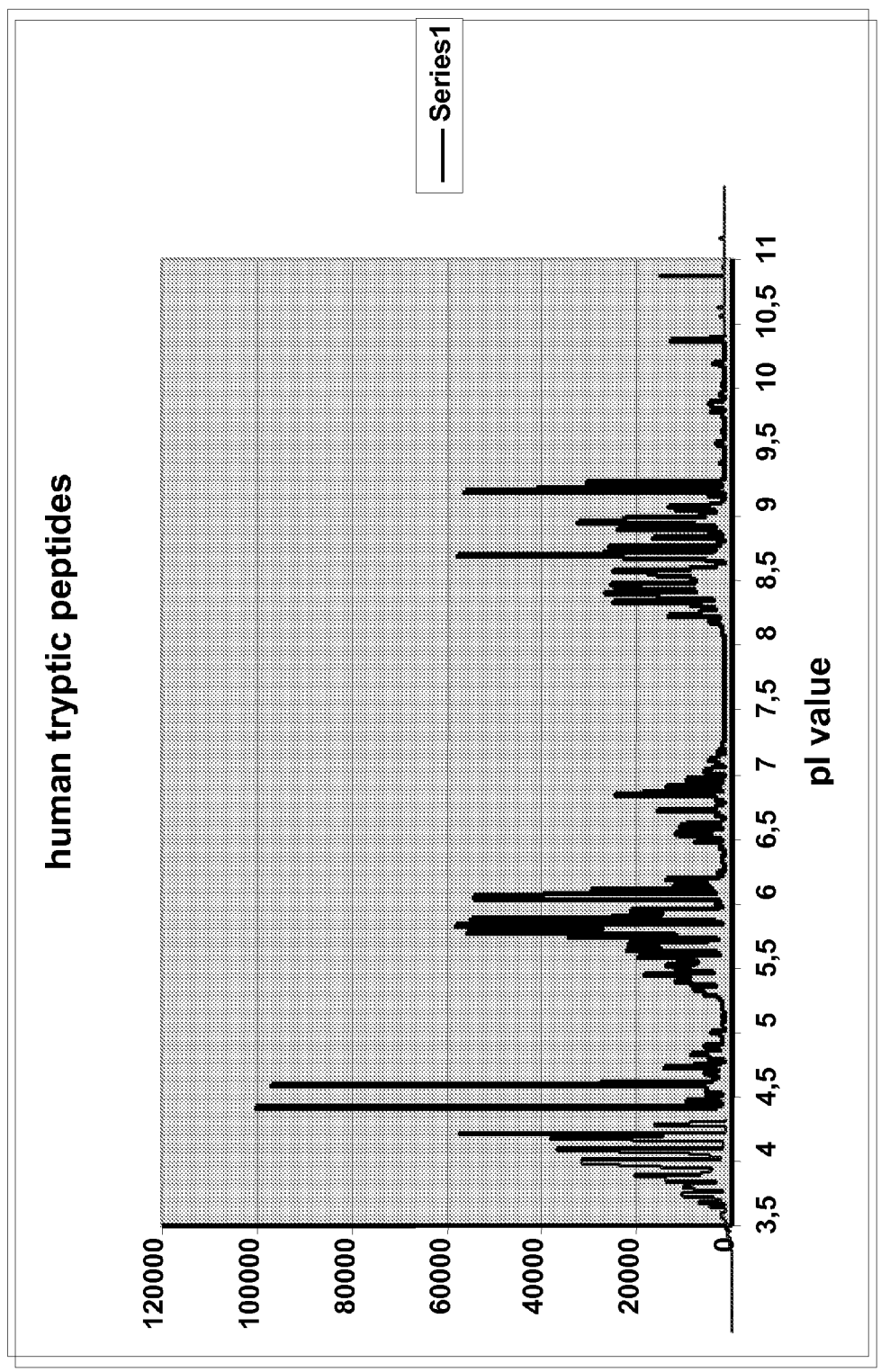
FIG. 1 is a diagram showing the pI distribution resulting from an in-silico tryptic digestion of all proteins possible to express from the human genome database and pI predictions for the resulting peptides using the above reference.

As shown in FIG. 1 human tryptic peptides originating from human proteins are unevenly along the x-axis representing their pI value.

Figure 2:
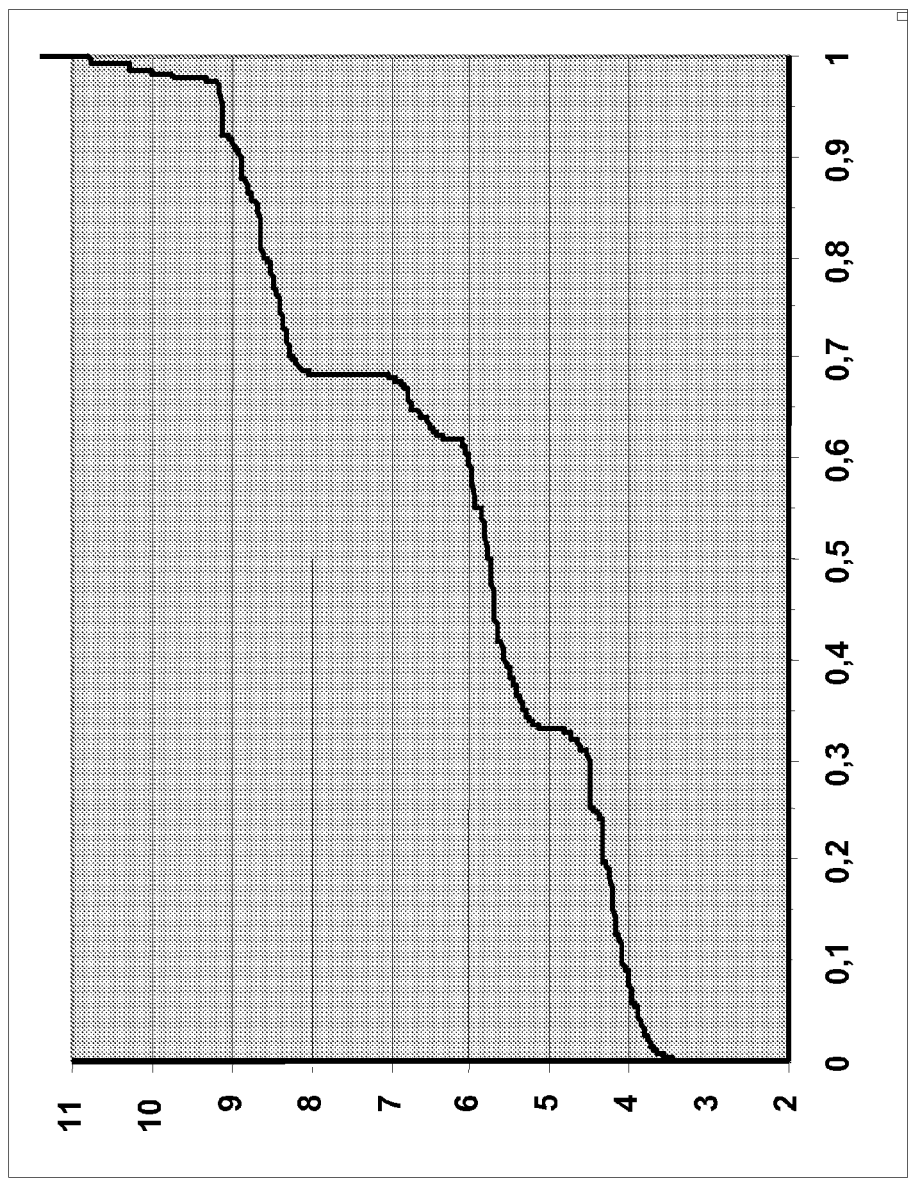
FIG. 2 shows a pH gradient resulting in even peptide distribution as function of distance, wherein anode is designated with (0) and cathode with (1)
Figure 3:
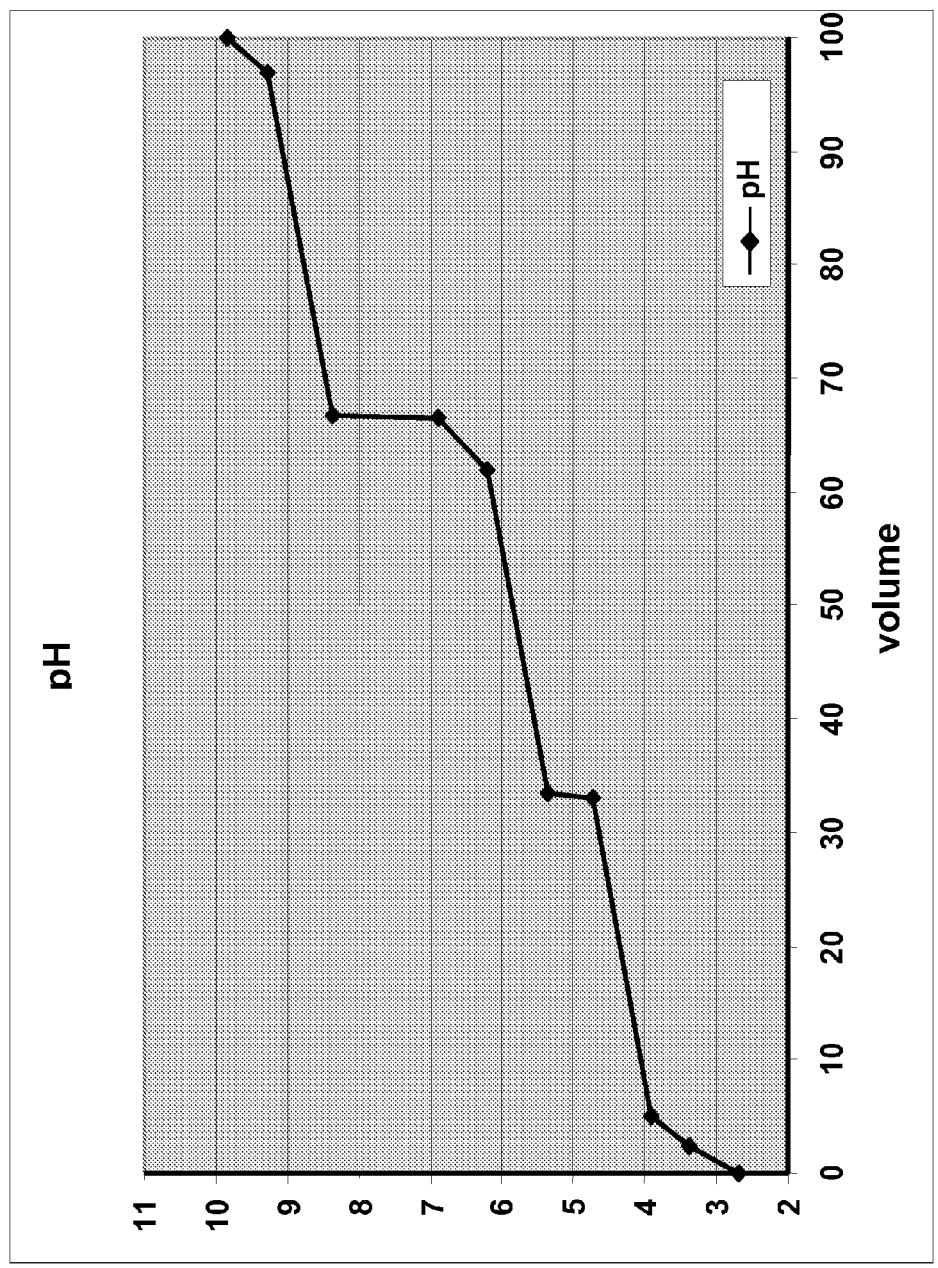
FIG. 3 shows a graph for generation of optimal pH gradient for tryptic peptides.

According to the present invention, an uneven pH-gradient, see FIG. 2, should be immobilised in an IEF gel or strip which will result in an even distribution of tryptic peptides after isoelectric focusing. In FIG. 3 it is shown how to produce such an uneven pH-gradient.

The gels according to the invention are cast to a thickness of approximately 0.5 mm.

The gels may be cast to achieve the three separate pH-intervals in one gel. Alternatively, the gel may be cast as three separate gel portions, each representing the separate pH-interval, which thereafter are joined to form a continuous gel. The separate pieces could to for example be joined with polyacrylamide bridges.

For better resolution of peptides the gel is optionally dried and re-swollen to less than 0.5 mm thickness. In a preferred embodiment, the gel is cast to a volume of 388 µl (gel dimensions 22 cm×3.3 mm), dried, and rehydrated to a volume of 250 µl.

Besides the improved resolution in the thinner gel, the decrease of diffusion after finished focusing is a further advantage as this allows use of longer times for scanning and handling of the strips prior to peptide extraction. The decreased thickness allows higher voltages and the increased polymer content also decreases the conductivity of the strip, which allows further improvement of resulting resolution by additional increase of the used voltage.

The IEF gel according to the invention comprising at least three non-linear pH-intervals is loaded with samples and run under the similar conditions as a conventional IEF gel.

After focusing the peptide resolution is high and the peptides are evenly distributed in the gel.

When the peptides are extracted from the gel, they are evenly distributed in the extracted fractions instead of having several peptides in some extracted fractions and zero peptides in other fraction. Thus, the present invention enables extraction of single peptides, or very few peptides, in the extracted fractions from the gel for later identification.

The above examples illustrate specific aspects of the present invention and are not intended to limit the scope thereof in any respect and should not be so construed. Those skilled in the art having the benefit of the teachings of the present invention as set forth above, can effect numerous modifications thereto. These modifications are to be construed as being encompassed within the scope of the present invention as set forth in the appended claims.

The invention claimed is:

1. A method for isoelectric focusing on a continuous gel characterized as including a pH gradient, comprising (i) loading an unknown peptide sample onto said gel and (ii) immobilizing on said continuous gel a non-linear pH gradient including at least three separate stepwise, and in relation to each other, not overlapping and not immediately adjacently arranged pH-intervals, under conditions favoring the even distribution of the peptides along the gel after isoelectric focusing, wherein said gel is adopted to peptides obtained by tryptic digestion of proteins.

2. The method of claim 1, wherein the gel is pre-cast.

3. The method of claim 1, wherein the gel is dried.

4. The method of claim 3, further comprising rehydrating the gel to less than its original wet thickness.

5. The method of claim 4, wherein the gel is rehydrated to 40-90% of its original wet thickness.

6. The method of claim 5, wherein the gel is rehydrated to 60% of its original wet thickness.

* * * * *